United States Patent [19]

Tsukuno et al.

[11] Patent Number: 5,312,947
[45] Date of Patent: May 17, 1994

[54] SILOXANE PURIFICATION

[75] Inventors: Akihito Tsukuno, Annaka; Isao Watanuki, Kanra; Makoto Sato, Annaka; Masaru Suzuki, Usui; Masao Maruyama, Usui; Masaaki Furuya, Usui, all of Japan

[73] Assignee: Shin-Etsu Chemical Co., Ltd., Tokyo, Japan

[21] Appl. No.: 125,274

[22] Filed: Sep. 23, 1993

[30] Foreign Application Priority Data

Sep. 24, 1992 [JP] Japan .................................. 4-279518

[51] Int. Cl.$^5$ .............................................. C07F 7/08
[52] U.S. Cl. .................................... 556/456; 556/450; 556/453
[58] Field of Search ........................ 556/450, 453, 456

[56] References Cited

U.S. PATENT DOCUMENTS

| | | | |
|---|---|---|---|
| 4,159,276 | 7/1979 | Desai et al. | 556/456 |
| 4,370,204 | 1/1983 | Kotzsch et al. | 556/456 |
| 4,661,612 | 4/1987 | George et al. | 556/453 |
| 4,774,346 | 9/1988 | Imai et al. | 556/456 |
| 4,962,221 | 10/1990 | Huntress et al. | 556/450 |
| 5,245,067 | 9/1993 | Schneider et al. | 556/466 |

Primary Examiner—Paul F. Shaver
Attorney, Agent, or Firm—Millen, White, Zelano & Branigan

[57] ABSTRACT

Siloxanes are purified by contacting siloxanes containing ionic crystals as an impurity with a polar solvent, evaporating the solvent, thereby increasing the mean particle size of the ion crystals, and removing the ion crystals from the siloxanes by filtration. The method enables brief, efficient purification of siloxanes in high yields, offering siloxanes having a minimal content of ionic crystals.

7 Claims, No Drawings

SILOXANE PURIFICATION

BACKGROUND OF THE INVENTION

1. Field of the Invention

This invention relates to purification of siloxanes, and more particularly, to a method of readily removing ionic crystal impurities from siloxanes.

2. Prior Art

One well-known prior art method for producing high molecular weight organopolysiloxanes is by converting relatively low molecular weight organopolysiloxanes into relatively high molecular weight organopolysiloxanes through polymerization in the presence of a catalyst. The catalysts used herein are basic substances, for example, potassium hydroxide, cesium hydroxide, quaternary ammonium hydroxides, and quaternary phosphonium hydroxides. At the end of polymerization of organopolysiloxanes, there is obtained a crude product containing the catalyst. An acid donor such as ethylene chlorohydrin, trimethylchlorosilane, phosphoric acid, carbonic acid and propionic acid is added to the crude product to neutralize the basic substance as the catalyst for deactivation. A neutralization salt which may be an inorganic or organic salt is then formed as ionic crystals. Such ionic crystals are removed by washing or filtering the product. Organopolysiloxanes are purified in this way.

In the last stage, siloxanes are generally purified by admitting the siloxane product containing ionic crystals into a container with mechanical agitation means, adding an adsorbent (e.g., charcoal) or filtering aid (e.g., diatomaceous earth) to the product in an amount of several percents by weight, agitating the mixture at a certain temperature for a certain time, and separating and removing the adsorbent or filtering aid from the siloxanes. The same treatment may be continuously carried out using a fixed bed.

This purifying method, however, encounters an increased load in the filtration step intended for removal of the adsorbent or filtering aid. It is also accompanied by a substantial loss of siloxanes due to adhesion of siloxanes to the adsorbent or filtering aid and is less efficient in operation. The adsorbent or filtering aid used becomes an industrial waste which must be disposed of through a cumbersome treatment and is unwanted from environmental considerations. In practice, with this purifying method it is quite difficult to decrease the content of ionic crystals in siloxanes to a sufficiently low level. Therefore, this purifying method is very disadvantageous from the aspects of process, productivity, operation efficiency, environment, economy and quality.

Another method for purifying siloxanes known comprises adding more than about 10% by weight of water to siloxanes in a container, agitating the mixture at a certain temperature for a certain time, allowing the mixture to stand in a stationary state for incurring liquid-liquid separation into siloxanes and water, and thereafter separating the aqueous layer of liquid from the container. The procedure of these steps is done once or repeated two or more times until siloxanes are purified to a desired degree. It is also known that in order to promote the liquid-liquid separation into siloxanes and water, a suitable solvent such a isopropyl alcohol and toluene is added at this stage.

The purifying method mentioned just above, however, has the problem that it is very difficult in practice to achieve complete separation between the liquid of the aqueous layer and the siloxane. As a result, separation is incomplete and the siloxanes are recovered in lower yields. Also the method uses the vast amount of water, which increases a load for waste water disposal and is detrimental to the environment. The throughput of this method is so small that the method must be repeated in several batches, resulting in a lowering of productivity. It takes a long time to separate water from siloxanes, for example, at least one hour until a desired level of separation is achieved although the exact time depends on the properties of siloxanes to be purified and a scale of production. Further complete separation beyond this level is very difficult in practice. It is sometimes necessary to positively remove water using a dewatering agent such as sodium sulfate. Even when such positive removal of water is employed, it is still very difficult in practice to remove ionic crystals from siloxanes to a final trace level. Therefore, this purifying method is also very disadvantageous from the aspects of process, productivity, environment, economy and quality.

Where various organochlorosilanes alone or in admixture of two or more are converted through hydrolysis into cyclic, linear or branched organopolysiloxanes, the hydrolysis entails hydrochloric acid as a by-product. In order to remove the hydrochloric acid from the hydrolyzate at the end of hydrolysis, it is a common practice to subject the hydrolyzate to neutralizing water washing using a basic substance such as sodium carbonate. However, since it is very difficult to completely remove from the hydrolyzate the neutralization salt resulting from neutralizing water washing by using the aforementioned purifying method, and since it is impossible in fact to remove the neutralization salt to a final trace level, some neutralization salt often remains in the hydrolyzate. There is a problem that the presence of such residual neutralization salt can adversely affect the properties of the hydrolyzate. Removing the neutralization salt as much as possible requires increased cost and energy.

As discussed above, the prior art siloxane purifying methods suffer from the problem that ionic crystals are left in siloxanes to detract from the physical properties of siloxanes required in various applications including outer appearance, heat resistance, and electrical properties.

SUMMARY OF THE INVENTION

Therefore, an object of the present invention is to provide a novel and improved siloxane purifying method capable of readily removing ionic crystals from siloxanes.

We have found that when a siloxane crude product containing ionic crystals (inorganic or organic salts) as an impurity is contacted with a polar solvent such as water, dimethyl sulfoxide and methanol, and the solvent is then evaporated therefrom, the particle size of the ion crystals is increased to several tens to several hundred times the original particle size. Such enlarged ionic crystals can be readily removed by filtration without substantial clogging of the filter or a substantial pressure loss across the filter.

Accordingly the present invention provides a method for purifying siloxanes comprising the steps of: contacting a siloxane crude product containing ionic crystals as an impurity with a polar solvent, then evaporating the solvent, thereby increasing the mean particle size of the ion crystals, and filtering the siloxane crude product for separating and removing the ion crystals therefrom.

DETAILED DESCRIPTION OF THE INVENTION

The siloxanes to which the purification method of the invention is applicable include cyclic polysiloxanes of the following formula (1) and/or mixtures of such polysiloxanes; linear polysiloxanes of the following formula (2) and/or mixtures of such polysiloxanes; polysiloxanes of the following formula (3) and/or mixtures of such polysiloxanes; and other siloxanes which do not detract from their physical properties upon contact with polar solvents to be described later. These siloxanes may be present alone or in admixture of two or more in a crude product.

$$(R_2{}^1SiO)_n \qquad (1)$$

In formula (1), $R^1$ is a substituted or unsubstituted monovalent hydrocarbon radical, preferably having 1 to 8 carbon atoms, for example, an alkyl radical, cycloalkyl radical, alkenyl radical, aryl radical, alkaryl radical, aralkyl radical, halogenated alkyl radical, and halogenated aryl radical. The radicals represented by $R^1$ may be either identical or different. Letter n is an integer of at least 3.

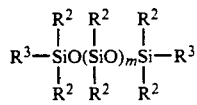

$$\begin{array}{c} R^2 \quad R^2 \quad R^2 \\ | \quad\ \ | \quad\ \ | \\ R^3-\text{SiO}(\text{SiO})_m\text{Si}-R^3 \\ | \quad\ \ | \quad\ \ | \\ R^2 \quad R^2 \quad R^2 \end{array} \qquad (2)$$

In formula (2), $R^2$ is a monovalent organic radical, preferably having 1 to 8 carbon atoms, for example, a radical as defined for $R^1$, an amino-containing radical, and a mercapto-containing radical. The radicals represented by $R^2$ may be either identical or different. $R^3$ is a radical as defined for $R^2$, hydroxyl radical, alkoxy radical having 1 to 8 carbon atoms or chloro radical. The radicals represented by $R^3$ may be either identical or different. Letter m is equal to 0 or a positive integer.

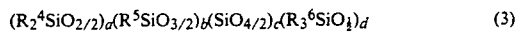

$$(R_2{}^4SiO_{2/2})_a(R^5SiO_{3/2})_b(SiO_{4/2})_c(R_3{}^6SiO_1)_d \qquad (3)$$

In formula (3), $R^4$, $R^5$, and $R^6$ are as defined for $R^3$ and they may be either identical or different. Letters a, b, c, and d are equal to 0 or positive integers, with the proviso that at least one of them is a positive integer of at least 1.

The purification method of the invention can remove from siloxanes ionic crystals which are soluble in polar solvents. Exemplary ionic crystals are solids of electrolyte salts including inorganic and organic salts. Examples of the inorganic salt include chlorides such as lithium chloride, sodium chloride, potassium chloride, cesium chloride, magnesium chloride and calcium chloride; carbonates such as potassium carbonate and sodium carbonate; borates such as potassium metaborate and sodium metaborate; sulfates such as potassium sulfate and sodium sulfate; nitrates such as potassium nitrate and sodium nitrate; and phosphates such as potassium phosphate and sodium phosphate. Exemplary of the organic salt are carboxylates such as potassium formate, potassium acetate, and potassium propionate; quaternary phosphonium salts such as tetra-n-butylphosphonium chloride; and quaternary ammonium salts such as tetramethylammonium chloride.

According to the siloxane purification method of the invention, a siloxane crude product is first contacted with a polar solvent. The polar solvent should preferably have a high dielectric constant of at least 30 and its molecule have an increased electric dipole moment. Included are protonic polar solvents such as methanol and ethanol, aprotic polar solvents such as dimethyl sulfoxide, and water. Water may be liquid water or water vapor. A choice of the solvent depends on the type of ionic crystals to be removed. In general, the use of a polar solvent in which ionic crystals are soluble to the maximum is commercially advantageous because the ionic crystals can be removed in the most efficient manner.

The siloxane purification method of the invention is described in the order of successive steps. A container, preferably a vacuum and/or pressure container which is equipped with a mechanical agitator is first charged with a siloxane crude product containing ionic crystals as an impurity. After the siloxane crude product is contacted with a polar solvent in the container, the polar solvent is evaporated and the remaining product is passed through a filter. The stage of introducing the polar solvent is not critical. The polar solvent can be admitted into the container together with the siloxane crude product. Alternatively, the polar solvent may be admitted into the container as the container with the siloxane charge is heated or after the container has reached an appropriate temperature and pressure.

The temperature, pressure and the type and quantity of polar solvent may be determined by taking into account various parameters including the physical and chemical properties of siloxanes themselves and the nature and content of ionic crystals contained therein. The temperature and pressure conditions should preferably be selected to ensure sufficient contact between the polar solvent and the ionic crystals and thereafter, the type and quantity of polar solvent are selected so as to ensure that ionic crystals are fully dissolved and extracted to the polar solvent component. In general, the amount of polar solvent used is selected in the range of about 1 to 5% by weight of the siloxane crude product when it contains about 5 to 500 ppm of ionic crystals. Use of a larger amount of solvent is not objectionable, but use of an excessive amount is not recommended because removal of the solvent from the siloxanes becomes cumbersome. Therefore, the amount of the polar solvent used should preferably be the necessary minimum amount to ensure an efficient siloxane purification process.

For example, for dimethylpolysiloxane containing about 20 ppm of potassium chloride crystals, the solvent may be selected from water and dimethyl sulfoxide. Satisfactory results are obtained in practice by using the solvent in an amount of a few percents by weight based on the weight of the dimethylpolysiloxane.

The step to be taken after the siloxane crude product is contacted with the polar solvent varies depending on the particular type of polar solvent used. Where water vapor is used, for example, it can be continuously introduced for a desired time at a predetermined temperature and pressure. Alternatively, water vapor is introduced at a predetermined temperature until a predetermined pressure is reached and thereafter, the system is closed and the contents are agitated and mixed for a predetermined time. Where an organic polar solvent or water is added, the system is closed and the contents are agitated and mixed for a predetermined time at a predetermine temperature and pressure.

The temperature, pressure and time may be determined over a wide range by taking into account various parameters including the physical and chemical properties of siloxanes themselves and the nature and content of ionic crystals contained therein. The temperature, pressure and time should preferably be selected to ensure sufficient contact between water vapor, water or polar solvent and the ionic crystals in siloxanes.

In general, satisfactory contact, dissolution and extraction of ionic crystals in the polar solvent favor higher temperatures and longer times. The pressure may be approximately atmospheric pressure in most cases although higher pressure are generally preferred. Preferred conditions include a temperature of from room temperature to about 200° C., preferably 50° to 150° C., a pressure of 1 to 10 atmospheres, preferably 1 to 2, and a time of about 1 to 180 minutes, preferably 30 to 60 minutes. Where the solvent is selected from water and dimethyl sulfoxide for dimethylpolysiloxane containing about 20 ppm of potassium chloride crystals, for example, satisfactory results are obtained in practice by continuing contact for about several minutes to several tens of minutes at a temperature of about 100° C. and approximately atmospheric pressure, with some variations in accordance with the amount of the solvent.

On contact with the solvent, it is quite advantageous to use an effective agitation means for maximizing the degree of mixing. Such agitation means may be mechanical one. It is also effective to purge an inert gas such as nitrogen into the system so as to achieve most efficient mixing.

At the end of the contacting step mentioned above, the polar solvent is evaporated off from the system at a predetermined temperature and pressure. At this point, it is possible to purge the polar solvent with an inert gas such as nitrogen.

The temperature and pressure at which the polar solvent is evaporated off may be determined over a wide range by taking into account various parameters including the physical and chemical properties of siloxanes themselves and the nature and content of ionic crystals contained therein. A choice of temperature and pressure may be made so as to maximize the particle size of ionic crystals and narrow the particle size distribution. Differently stated, as these conditions vary, the ionic crystals in siloxanes largely change their mean particle size, particle size distribution, and shape. It is then necessary and recommended in actual operation to determine optimum conditions through experimentation. In general, the conditions include a temperature of from room temperature to about 200° C., preferably 50° to 150° C., and a pressure of 0.1 to 1 atmosphere, preferably 0.5 to 1. Where water is selected as the solvent for dimethylpolysiloxane containing about 20 ppm of potassium chloride crystals, for example, satisfactory results are obtained in practive by evaporating water at a temperature of about 130° C. and a pressure of about 300 mmHg, with some variations in accordance with the amount of water.

By purifying siloxanes in this way, there is obtained a pure siloxane product having minimized impurity contents, for example, a potassium (K) content of less than 0.1 ppm, a sodium (Na) content of less than 0.5 ppm, and a chlorine (Cl) content of less than 1.0 ppm.

EXAMPLE

Examples of the present invention are given below by way of illustration and not by way of limitation.

EXAMPLE 1

A vacuumizable/autoclave pressurizable container equipped with a mechanical stirrer was charged with 1,800 kg of octamethyltetracyclosiloxane and 204 kg of methylpolysiloxane of the following formula (4):

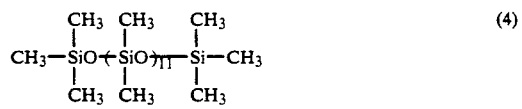

The container was heated to an interior temperature of 165° to 175° C. To the siloxane mixture was added 50 ppm of potassium hydroxide. Polymerization was effected for 4 hours at a temperature of 165° to 175° C. and atmospheric pressure. To the resulting polysiloxane was added trimethylchlorosilane as a neutralizing agent in an amount three times the neutralization equivalent to the amount of potassium hydroxide. With the container closed, neutralization reaction was effected for one hour at a temperature of 165° to 175° C.

There was obtained a polysiloxane crude product having a viscosity of 203 centistokes at 25° C., a heat loss of 13.5% (when heated at 105° C. for 3 hours) and a potassium (K) content of 34.6 ppm.

The container was adjusted to an interior temperature of 165° to 175° C. under atmospheric pressure before steam under a pressure of 5 kg/cm.G was fed to the container for one hour at a rate of 3% by weight per hour based on the weight of the polysiloxane crude product. As steam was fed, cyclic polysiloxanes mainly including octamethyltetracyclosiloxane, steam and excess trimethylchlorosilane distilled out of the container into a water cooled condenser connected to the container top where they were quickly condensed and discharged outside the container.

After a predetermined amount of steam was fed, the container was adjusted to an interior temperature of 165° to 175° C. under atmospheric pressure. Through the polysiloxanes in the container, nitrogen gas was passed for 30 minutes at a rate of 2 Nm$^3$/hr. to purge steam, thereby removing the steam and dissolved water from the system. Finally, the product was filtered and purified using a filter press under a filtration pressure of 2 kg/cm$^2$, yielding purified dimethylpolysiloxane. The time taken for filtration and purification was 4 hours.

The polysiloxane resulting from this purification process had a viscosity of 261 centistokes at 25° C., a heat loss of 5.5% (when heated at 105° C. for 3 hours) and a potassium (K) content of less than 0.1 ppm.

COMPARATIVE EXAMPLE 1

Using the same container, starting reactants, polymerization catalyst, and neutralizing agent as in Example 1, polymerization and neutralization were similarly carried out to yield a similar polysiloxane crude product.

The crude product was subjected to vacuum stripping for one hour at a temperature of 120° to 130° C. and a pressure of 1 to 10 mmHg. The product was filtered and purified as in Example 1, yielding purified dimethylpolysiloxane. The time taken for filtration and purification was 40 hours.

The polysiloxane resulting from this purification process had a viscosity of 265 centistokes at 25° C., a heat loss of 5.4% (when heated at 105° C. for 3 hours) and a potassium (K) content of 8.5 ppm.

EXAMPLE 2

A container as used in Example 1 was charged with 2,000 kg of octamethyltetracyclosiloxane and 104 kg of methylpolysiloxane of formula (4) shown above. The container was heated to an interior temperature of 165° to 175° C. To the siloxane mixture was added 200 ppm of potassium hydroxide. Polymerization was effected for 4 hours at a temperature of 165° to 175° C. and atmospheric pressure. To the resulting polysiloxane was added ethylene chlorohydrin as a neutralizing agent in an amount three times the neutralization equivalent to the amount of potassium hydroxide. With the container closed, neutralization reaction was effected for one hour at a temperature of 165° to 175° C.

There was obtained a polysiloxane crude product having a viscosity of 894 centistokes at 25° C., a heat loss of 13.6% (when heated at 105° C. for 3 hours) and a potassium (K) content of 139.0 ppm.

To the polysiloxane crude product was added 2.5% by weight of water. For aging, the container was maintained for 30 minutes at an interior temperature of 100° to 110° C. under atmospheric pressure. Thereafter, water was removed from within the container under the conditions: a pressure of 250 to 350 mmHg and a temperature of 125° to 135° C. As water was removed, cyclic polysiloxanes mainly including octamethyltetracyclosiloxane and excess ethylene chlorohydrin distilled out of the container into a water cooled condenser connected to the container top where they were quickly condensed and discharged outside the container.

Finally, the product was filtered and purified using a filter press under a filtration pressure of 2 kg/cm², yielding purified dimethylpolysiloxane.

The polysiloxane resulting from this purification process had a viscosity of 1,162 centistokes at 25° C., a heat loss of 5.0% (when heated at 105° C. for 3 hours) and a potassium (K) content of less than 0.1 ppm.

COMPARATIVE EXAMPLE 2

Using the same container, starting reactants, polymerization catalyst, and neutralizing agent as in Example 2, polymerization and neutralization were similarly carried out to yield a similar polysiloxane crude product.

The crude product was filtered and purified as in Example 2, yielding purified dimethylpolysiloxane.

The polysiloxane resulting from this purification process had a viscosity of 900 centistokes at 25° C., a heat loss of 13.4% (when heated at 105° C. for 3 hours) and a potassium (K) content of 34.0 ppm.

EXAMPLE 3

A container as used in Example 1 was charged with 1,800 kg of octamethyltetracyclosiloxane and 19 kg of tetramethyldivinyldisiloxane of the following formula (5).

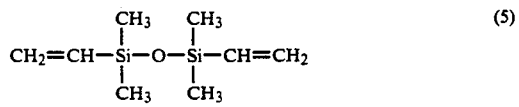

$$CH_2=CH-\underset{\underset{CH_3}{|}}{\overset{\overset{CH_3}{|}}{Si}}-O-\underset{\underset{CH_3}{|}}{\overset{\overset{CH_3}{|}}{Si}}-CH=CH_2 \quad (5)$$

The container was heated to an interior temperature of 130° to 140° C. To the siloxane mixture was added 50 ppm of potassium hydroxide. Polymerization was effected for 8 hours at a temperature of 130° to 140° C. and atmospheric pressure. To the resulting polysiloxane was added ethylene chlorohydrin as a neutralizing agent in an amount three times the neutralization equivalent to the amount of potassium hydroxide. With the container closed, neutralization reaction was effected for two hours at a temperature of 130° to 140° C.

There was obtained a polysiloxane crude product having a viscosity of 659 centistokes at 25° C., a heat loss of 14.0% (when heated at 105° C. for 3 hours) and a potassium (K) content of 34.6 ppm.

To the polysiloxane crude product was added 2.5% by weight of water. For aging, the container was maintained for 30 minutes at an interior temperature of 100° to 110° C. under atmospheric pressure. Thereafter, water was removed from within the container under the conditions: a pressure of 250 to 350 mmHg and a temperature of 125° to 135° C. As water was removed, cyclic polysiloxanes mainly including octamethyltetracyclosiloxane and excess ethylene chlorohydrin distilled out of the container into a water cooled condenser connected to the container top where they were quickly condensed and discharged outside the container. Finally, the product was cooled down to room temperature and filtered and purified using a filter press under a filtration pressure of 2 kg/cm², yielding purified vinyl-containing polysiloxane.

The polysiloxane resulting from this purification process had a viscosity of 995 centistokes at 25° C., a heat loss of 3.0% (when heated at 105° C. for 3 hours) and a potassium (K) content of less than 0.1 ppm.

COMPARATIVE EXAMPLE 3

Using the same container, starting reactants, polymerization catalyst, and neutralizing agent as in Example 3, polymerization and neutralization were similarly carried out to yield a similar polysiloxane crude product.

The crude product was filtered and purified as in Example 3, yielding purified vinyl-containing polysiloxane.

The polysiloxane resulting from this purification process had a viscosity of 670 centistokes at 25° C., a heat loss of 13.0% (when heated at 105° C. for 3 hours) and a potassium (K) content of 5.0 ppm.

EXAMPLE 4

Polysiloxane was polymerized as in Example 3. Carbon dioxide (CO₂) gas was bubbled into the polysiloxane for two hours at a temperature of 130° to 140° C. and atmospheric pressure for neutralizing and deactivating potassium hydroxide used as the polymerization catalyst.

There was obtained a polysiloxane crude product having a viscosity of 700 centistokes at 25° C., a heat loss of 14.0% (when heated at 105° C. for 3 hours) and a potassium (K) content of 34.6 ppm.

To the polysiloxane crude product was added 2.5% by weight of water. For aging, the container was maintained for 30 minutes at an interior temperature of 100° to 110° C. under atmospheric pressure. Thereafter, water was removed from within the container at a temperature of 125° to 135° C. and atmospheric pressure. As water was removed, cyclic polysiloxanes mainly including octamethyltetracyclosiloxane distilled out of the container into a water cooled condenser connected to the container top where they were quickly condensed and discharged outside the container. Finally, the product was cooled down to room temperature and filtered and purified using a filter press under a filtration pressure of 2 kg/cm², yielding purified vinyl-containing polysiloxane.

The polysiloxane resulting from this purification process had a viscosity of 1,057 centistokes at 25° C., a heat loss of 2.8% (when heated at 105° C. for 3 hours) and a potassium (K) content of less than 0.1 ppm.

COMPARATIVE EXAMPLE 4

Using the same container, starting reactants, polymerization catalyst, and neutralizing agent as in Example 4, polymerization and neutralization were similarly carried out to yield a similar polysiloxane crude product.

The crude product was filtered and purified as in Example 4, yielding purified vinyl-containing polysiloxane.

The polysiloxane resulting from this purification process had a viscosity of 705 centistokes at 25° C., a heat loss of 13.5% (when heated at 105° C. for 3 hours) and a potassium (K) content of 8.1 ppm.

EXAMPLE 5

Using the same container, starting reactants, polymerization catalyst, and neutralizing agent as in Example 2, polymerization and neutralization were similarly carried out to yield a similar polysiloxane crude product.

To the polysiloxane crude product was added 2.5% by weight of dimethyl sulfoxide. For aging, the container was maintained for 30 minutes at an interior temperature of 60° to 70° C. under atmospheric pressure. Thereafter, dimethyl sulfoxide was removed from within the container at a temperature of 190° to 200° C. and atmospheric pressure. As dimethyl sulfoxide was removed, cyclic polysiloxanes mainly including octamethyltetracyclosiloxane and excess ethylene chlorohydrin distilled out of the container into a water cooled condenser connected to the container top where they were quickly condensed and discharged outside the container. Finally, the product was filtered and purified using a filter press under a filtration pressure of 2 kg/cm², yielding purified dimethylpolysiloxane.

The polysiloxane resulting from this purification process had a viscosity of 1,250 centistokes at 25° C., a heat loss of 1.8% (when heated at 105° C. for 3 hours) and a potassium (K) content of less than 0.1 ppm.

EXAMPLE 6

Using the same container, starting reactants, polymerization catalyst, and neutralizing agent as in Example 2, polymerization and neutralization were similarly carried out to yield a similar polysiloxane crude product.

To the polysiloxane crude product was added 2.5% by weight of methanol. For aging, the container was maintained for 30 minutes at an interior temperature of 60° to 70° C. under atmospheric pressure. Thereafter, methanol was removed from within the container at a temperature of 120° to 130° C. and atmospheric pressure. As methanol was removed, cyclic polysiloxanes mainly including hexamethyltricyclosiloxane and excess ethylene chlorohydrin distilled out of the container into a water cooled condenser connected to the container top where they were quickly condensed and discharged outside the container. Finally, the product was filtered and purified using a filter press under a filtration pressure of 2 kg/cm², yielding purified dimethylpolysiloxane.

The polysiloxane resulting from this purification process had a viscosity of 1,050 centistokes at 25° C., a heat loss of 8.4% (when heated at 105° C. for 3 hours) and a potassium (K) content of less than 0.1 ppm.

EXAMPLE 7

Using the same container, starting reactants, and polymerization catalyst as in Example 2, polymerization was similarly carried out. To the resulting polysiloxane was added acetic acid as a neutralizing agent in an amount three times the neutralization equivalent to the amount of potassium hydroxide. With the container closed, neutralization reaction was effected for two hours at a temperature of 100° to 110° C.

There was obtained a polysiloxane crude product having a viscosity of 910 centistokes at 25° C., a heat loss of 13.5% (when heated at 105° C. for 3 hours) and a potassium (K) content of 139.0 ppm.

To the polysiloxane crude product was added 2.5% by weight of water. For aging, the container was maintained for 30 minutes at an interior temperature of 90° to 100° C. under atmospheric pressure. Thereafter, water was removed from within the container at a temperature of 120° to 130° C. and atmospheric pressure. As water was removed, cyclic polysiloxanes mainly including octamethyltetracyclosiloxane and excess acetic acid distilled out of the container into a water cooled condenser connected to the container top where they were quickly condensed and discharged outside the container. Finally, the product was filtered and purified using a filter press under a filtration pressure of 2 kg/cm², yielding purified dimethylpolysiloxane.

The polysiloxane resulting from this purification process had a viscosity of 1,138 centistokes at 25° C., a heat loss of 5.6% (when heated at 105° C. for 3 hours) and a potassium (K) content of less than 0.1 ppm.

COMPARATIVE EXAMPLE 5

Using the same container, starting reactants, polymerization catalyst, and neutralizing agent as in Example 7, polymerization and neutralization were similarly carried out to yield a similar polysiloxane crude product.

The crude product was filtered and purified as in Example 7, yielding purified dimethylpolysiloxane.

The polysiloxane resulting from this purification process had a viscosity of 915 centistokes at 25° C., a heat loss of 13.3% (when heated at 105° C. for 3 hours) and a potassium (K) content of 14.1 ppm.

EXAMPLE 8

A container as used in Example 1 was charged with 3,600 kg of water and adjusted to an interior temperature of 65° to 75° C. A chlorosilane premix consisting of 1,200 kg of dimethyldichlorosilane and 598 kg of diphenyldichlorosilane was added dropwise over one hour to the container at 65° to 75° C. and atmospheric pressure, and hydrolysis was continued for a further 30 minutes under the same conditions. Thereafter, the reaction mixture was allowed to stand for 30 minutes at 65° to 75° C. and atmospheric pressure, whereupon the lower layer of hydrochloric acid water was separated and removed. To the polysiloxane or hydrolyzate were added 2.5% by weight of water and 3,000 ppm of sodium carbonate. For aging, the container was maintained for 30 minutes at an interior temperature of 100° to 110° C. under atmospheric pressure. Thereafter, water was removed from within the container at a temperature of 125° to 135° C. and atmospheric pressure. As water was removed, cyclic polysiloxanes mainly including octamethyltetracyclosiloxane distilled out of the container into a water cooled condenser connected to the container top where they were quickly condensed and separated. Only the siloxanes were fed back to the system and water was discharged outside the container. Finally, the product was filtered and purified using a filter press under a filtration pressure of 2 kg/cm², yielding purified dimethyldiphenylpolysiloxane. From the amount of the product, the yield was calculated to be 99.0%.

The polysiloxane resulting from this purification process had a viscosity of 44.6 centistokes at 25° C., a heat loss of 30.7% (when heated at 105° C. for 3 hours) and a refractive index of 1.4775. It had a sodium (Na) content of less than 0.5 ppm and a chlorine (Cl) content of less than 1.0 ppm.

COMPARATIVE EXAMPLE 6

Using the same container and starting reactants as in Example 8, hydrolysis, static standing and hydrochloric acid water removal were carried out as in Example 8. To the hydrolyzate was added 30% by weight of water. The mixture was agitated and mixed for one hour at a temperature of 60° to 70° C. and atmospheric pressure, and then allowed to stand and separate into siloxane and water layers. This water washing step was repeated three times in total. Then using the same amount as above of water and 3% by weight of sodium carbonate based on the siloxanes, neutralizing water washing was carried out under the same conditions as above. The product was then dried using 5% by weight based on the siloxanes of anhydrous sodium sulfate as a dewatering agent. Finally, the product was filtered and purified using a filter press under a filtration pressure of 2 kg/cm², yielding purified dimethyldiphenylpolysiloxane. From the amount of the product, the yield was calculated to be 85.0%.

The polysiloxane resulting from this purification process had a viscosity of 45.0 centistokes at 25° C., a heat loss of 30.0% (when heated at 105° C. for 3 hours) and a refractive index of 1.4776. It had a sodium (Na) content of 100.5 ppm and a chlorine (Cl) content of 32.5 ppm.

EXAMPLE 9

The polysiloxane products of Examples 2, 4 and 5, both at the end of neutralization and at the end of neutralization and purification, were observed under a scanning electron microscope to determine the mean particle size of neutralization salt crystals in the polysiloxane products. The results are shown in Table 1.

TABLE 1

| Siloxane | Stage after | Mean particle size (μm) |
| --- | --- | --- |
| Example 2 | Neutralization | 0.8 |
|  | Purification | 110.0 |
| Example 4 | Neutralization | 0.5 |
|  | Purification | 62.0 |
| Example 5 | Neutralization | 0.8 |
|  | Purification | 90.0 |

It is evident from Table 1 that by purifying siloxanes containing neutralization salt crystals according to the present invention, the neutralization salt crystals grew up to a particle size of several ten to several hundred times the particle size before purification. Therefore, the ionic crystals can be readily removed by simple filtration to a final trace level.

The present invention enables purification of siloxanes within a short time, in high yields, and with high productivity, offering siloxanes having a minimal content of ionic crystals.

Although some preferred embodiments have been described, many modifications and variations may be made thereto in the light of the above teachings. It is therefore to be understood that within the scope of the appended claims, the invention may be practiced otherwise than as specifically described.

We claim:
1. A method for purifying siloxanes comprising
   contacting a siloxane crude product containing ionic crystals as an impurity with a polar solvent,
   evaporating the solvent from the crude product, thereby increasing the mean particle size of the ion crystals, and
   filtering the siloxane crude product for separating and removing the ion crystals therefrom.
2. The method of claim 1 wherein said polar solvent has a dielectric constant of at least 30.
3. The method of claim 1 wherein said polar solvent is water, dimethyl sulfoxide or methanol.
4. The method of claim 1, wherein the siloxane crude product comprises:
   one or more cyclic siloxanes of the formula (1),

$$(R_2^1 SiO)_n \tag{1}$$

wherein each $R^1$ is independently a halogen substituted or unsubstituted monovalent hydrocarbon radical having 1 to 8 carbon atoms, and n is an integer of 3 or more,
one or more linear siloxanes of the formula (2), $$R^3 - \underset{\underset{R^2}{|}}{\overset{\overset{R^2}{|}}{Si}} O(\underset{\underset{R^2}{|}}{\overset{\overset{R^2}{|}}{Si}} O)_m \underset{\underset{R^2}{|}}{\overset{\overset{R^2}{|}}{Si}} - R^3, \tag{2}$$

wherein each $R^2$ is independently a monovalent organic radical having 1 to 8 carbon atoms, each $R^3$ is independently a radical as defined for $R^2$, a hydroxyl radical, an alkoxy radical having 1 to 8 carbon atoms or a chloro radical, and m is 0 or a positive integer,
one or more polysiloxanes of the formula (3), $$(R_2^4 SiO_{2/2})_a (R^5 SiO_{3/2})_b (SiO_{4/2})_c (R_3^6 SiO_{1})_d \tag{3}$$

wherein each $R^4$, $R^5$ and $R^6$ are independently as defined for $R^3$, and letters a, b, c, and d are equal to 0 or positive integers, with the proviso that at least one of them is at least 1, or mixtures thereof.

5. The method of claim 1, wherein the ionic crystals comprise crystals of lithium chloride, sodium chloride, potassium chloride, cesium chloride, magnesium chloride, calcium chloride, potassium carbonate, sodium carbonate, potassium metaborate, sodium metaborate, potassium sulfate, sodium sulfate, potassium nitrate, sodium nitrate, potassium phosphate, sodium phosphate, potassium formate, potassium acetate, potassium propionate, tetra-n-butylphosphonium chloride, or tetramethylammonium chloride.

6. The method of claim 1, wherein the siloxane crude product contains 5 to 500 ppm by weight of ionic crystals and the polar solvent is used in an amount of 1 to 5% by weight of the siloxane crude product.

7. The method of claim 1, wherein the siloxane crude product is contacted with the polar solvent at a temperature of 50° to 200° C. and a pressure of 1 to 10 atmospheres.

* * * * *